(12) United States Patent
Prinderre et al.

(10) Patent No.: US 9,060,930 B2
(45) Date of Patent: Jun. 23, 2015

(54) PROCESS FOR MAKING GASTRORETENTIVE DOSAGE FORMS

(75) Inventors: Pascal Prinderre, Marseilles (FR); Christophe Sauzet, Aix En Provence (FR)

(73) Assignee: UNIVERSITE DE LA MEDITERRANEE, Marseilles (FR)

( * ) Notice: Subject to any disclaimer, the term of this patent is extended or adjusted under 35 U.S.C. 154(b) by 0 days.

(21) Appl. No.: 12/997,092

(22) PCT Filed: Jun. 8, 2009

(86) PCT No.: PCT/IB2009/005889
§ 371 (c)(1),
(2), (4) Date: Mar. 7, 2011

(87) PCT Pub. No.: WO2009/150514
PCT Pub. Date: Dec. 17, 2009

(65) Prior Publication Data
US 2012/0021009 A1   Jan. 26, 2012

(30) Foreign Application Priority Data
Jun. 9, 2008 (EP) ................. 08290529

(51) Int. Cl.
*A61K 9/00* (2006.01)
*A61K 31/65* (2006.01)
*A61K 31/522* (2006.01)
*B02C 19/00* (2006.01)

(52) U.S. Cl.
CPC .................. *A61K 9/0065* (2013.01)

(58) Field of Classification Search
None
See application file for complete search history.

(56) References Cited

U.S. PATENT DOCUMENTS

| 4,814,179 | A | 3/1989 | Bolton et al. |
| 4,844,905 | A | 7/1989 | Ichikawa et al. |
| 5,626,876 | A | 5/1997 | Müller et al. |
| 2006/0013876 | A1 * | 1/2006 | Lohray et al. ............ 424/472 |
| 2007/0269512 | A1 * | 11/2007 | Wang et al. ............. 424/468 |

FOREIGN PATENT DOCUMENTS

| EP | 0 235 718 | | 9/1987 |
| EP | 0297978 | A2 | 1/1989 |
| EP | 0539059 | A1 | 4/1993 |
| EP | 2182917 | B1 * | 7/2011 |
| JP | 2001270827 | A | 10/2001 |
| WO | WO 89/06956 | | 8/1989 |
| WO | WO 01/58424 | | 8/2001 |
| WO | WO 0158424 | A1 * | 8/2001 |

OTHER PUBLICATIONS

MSDS for 0.1M Hydrochloric acid solution downloaded on Jul. 23, 2012 from the site: http://www.sigmaaldrich.com/MSDS/MSDS/DisplayMSDSPage.do?country=US&language=en&productNumber=84434&brand=SIGMA&PageToGoToURL=http%3A%2F%2Fwww.sigmaaldrich.com%2Fcatalog%2Fproduct%2Fsigma%2F84434%3Flang%3Den.*
Sherif I. Farag Badawy, David B. Gray, and Munir A. Hussain. A Study on the Effect of Wet Granulation on Microcrystalline Cellulose ParticleStructure and Performance. Pharmaceutical Research, vol. 23, No. 3, Mar. 2006.*
Sherif I. Farag Badawy, David B. Gray, and Munir A. Hussain. A Study on the Effect of Wet Granulation on Microcrystalline Cellulose Particle Structure and Performance. Pharmaceutical Research, vol. 23, No. 3, Mar. 2006.*
Michelle K. Papp & Chetan P. Pujara & Rodolfo Pinal. Monitoring of High-shear Granulation using Acoustic Emission: Predicting Granule Properties. J Pharm Innov (2008) 3:113-122.*

* cited by examiner

*Primary Examiner* — Frederick Krass
*Assistant Examiner* — Michael P Cohen
(74) *Attorney, Agent, or Firm* — Harness, Dickey & Pierce, P.L.C.

(57) ABSTRACT

The present disclosure relates to a novel process for making oral solid gastro-retentive forms, including the steps of providing a powder mixture including a hydrophobic powder, overgranulating this powder mixture with a granulating solution into an overgranulated paste, and drying all paste into a solid, as well as to pharmaceutical solid dosage forms which are retained in the stomach or upper gastrointestinal tract for a controlled delivery of a drug.

20 Claims, 4 Drawing Sheets

PROCESS FOR MAKING GASTRORETENTIVE DOSAGE FORMS

CROSS-REFERENCE TO RELATED APPLICATIONS

This application is a National Phase Entry of International Application No. PCT/IB2009/005889, filed on Jun. 8, 2009, which claims priority to European Application Serial No. 08290529.0, filed on Jun. 9, 2008, both of which are incorporated by reference herein.

FIELD OF THE INVENTION

The present invention relates to novel pharmaceutical compositions which are retained in the stomach or upper gastrointestinal tract for a controlled delivery of a drug. The present invention also provides methods of preparation as well as methods of using these dosage forms in therapeutic treatments.

BACKGROUND

Therapeutic agents see their efficiency intimately related to their method of administration. When taken orally, a drug interacts with specific absorption sites located in different portions throughout the gastrointestinal tract (GI), resulting in that certain agents are only absorbed in the stomach, the upper or lower intestine. Therefore, because the drugs are not absorbed uniformly all over the length of the GI tract, the rate of absorption may not be constant and does not allow a most efficient treatment. These may significantly be improved when the method of administration provides a controlled delivery of the active ingredient towards the only implicated sites.

For example, it may be significant to prolong the residence time specifically in the stomach in the case of drugs which are only locally active such as anti-acids, have an absorption window in the stomach or in the upper intestine such as L-Dopa or riboflavin, are unstable in the intestinal or colonic environment such as captopril or exhibit low solubility at high pH values such as diazepam, or verapamil. This may be also important in treatments of micro-organisms, which colonize the stomach since the three main factors reducing luminal delivery of drugs to them are gastric emptying, gastric acidity and the epithelial mucus layer. These forms may also be used to release a biomarker to monitor and identify gastric conditions.

While the existing immediate release forms provide the disadvantage of repeated administration of a medicament as well as fluctuations in drug plasma levels, controlled drug delivery systems were significantly developed. They allow the delivery of a therapeutic agent in such way that the level of the drug is maintained within a particular window as long as the form continues to deliver the drug at a constant rate. Also, apart from reducing the required frequency of administration or maintaining safe blood levels, there are other benefits associated with the intake of controlled release forms such as the reduction of the severity of side effects.

A large variety of controlled release forms have already been disclosed, as summarized in "*Gastroretentive drug delivery systems*", by Alexander Streubel, Juergen Siepmann & Roland Bodmeier, *Expert Opin. Drug Deliv.* (2006) 3(2): 217-233, or in "*Gastroretentive dosage forms: Overview and special case of Helicobacter Pylori*", *J. Control. Rel.*, 111 (2006) 1-18 by Bardonnet et al. They are based on different modes of operation and accordingly have been variously named, for example, as dissolution controlled systems, diffusion controlled systems, ion exchange resins, osmotically controlled systems, erodible matrix systems, pH independent formulations, bioadhesive forms, low density systems, swelling forms and the like.

The low density systems particularly, float once in contact with the gastric juice and allow prolonged residence time into the stomach by preventing premature emptying through the pylorus. They are usually made of biodegradable materials which disintegrate after a determined period of time and the residual form is then eventually emptied from the stomach. Floating properties of drug delivery systems can be based on several principles, including inherent low density, low density due to swelling or to gas generation.

The swelling systems for example, not only see their size increase above the diameter of the pylorus which results from the unfolding of complex geometric shapes, or the expansion of swellable excipients, but also see their density decrease to provide floating properties. For the gas generating systems, the low density is obtained from the formation of carbon dioxide within the device following contact with body fluids. Some of these dosage forms already exist and usually associate both swelling and gas generation phenomena. Some of them are currently being tested clinically such as Cipro XR®, Xatral® OD, or have already received the approval of a Drug Regulatory Administration such as Glumetza® or Proquin XR®. They however have the draw back not to float directly following the administration, as it takes time for the systems to reach the desired size, and even longer when it is an effervescent form because of the gas generation process.

More advantageously, in inherent low density systems the floating properties are provided since the beginning and swallowing, allowing for substantially no lag time. They are generally provided by entrapment of air, incorporation of low density materials, with foam powders, or combinations thereof. For example, Desai and Bolton in U.S. Pat. No. 4,814,179 developed a moulded agar gel tablet with oil and air, which replaced evaporated water following drying. The process for manufacturing involves the steps of forming an emulsion, from an oily composition of the active and an aqueous solution of agar gel. The emulsion is poured into a mould and subsequently dried. Krögel and Bodmeier proposed in "*Development of a multifunctional matrix drug delivery system surrounded by an impermeable cylinder*", *J. Control. Release* (1999) 61:43-50, a floating device consisting of an impermeable hollow polypropylene cylinder, containing two drug matrix tablets, each of them closing one end of the cylinder, so that an air-filled space was created in between, resulting in a low density system.

More recently, developments led to single unit and multiparticulate systems containing highly porous polypropylene foam powder and matrix forming polymers, which are said to provide a low density, excellent in vitro floating behaviour and broad spectrum of release patterns. See for example WO 89/06956, disclosing a floating drug wherein a porous structural element, such as a foam or a hollow body is placed within a matrix, and optionally compressed into a tablet dosage form. See also Streubel, Siepmann & Bodmeier, "*Floating matrix tablets based on low density foam powder*", *Eur. J. Pharm. Sci.* (2003) 18:37-45, or *Int. J. Pharm.* (2002) 241: 279-292, which provides examples of such matrix forming polymers: hydroxypropyl methylcellulose, polyacrylates, sodium alginates, corn starch, carrageenan, gum guar, gum arabic, Eudragit®RS, ethyl cellulose, or poly methyl methacrylate.

Another multiple unit gastroretentive drug delivery system containing air compartments was disclosed by Iannucelli et al., wherein each single unit consisted of a calcium alginate core, separated by an air compartment formed during a drying step, from a calcium alginate or calcium alginate/polyvinyl alcohol membrane. It is said to show both good in vitro and in vivo buoyancy behaviour and suitable drug release patterns were observed when both the core and the membranes were loaded with a solid dispersion of drug/polyvinylpyrrolidone. Finally, some other bead formulations containing air compartment were developed by incorporation of air bubble and air filled hollow spaces within the system. These are disclosed by Bulgarelli et al., in "*Effect of matrix composition and process conditions on casein-gelatin beads floating properties*", Int. J. Pharm. (2000) 198:157-165, and by Talukder et Fassihi, "*Gastroretentive delivery systems: hollow beads*", Drug Dev. Ind. Pharm. (2004) 30:405-412. Floating properties however depend on the filling state of the stomach.

Most of the above compositions incorporate air into the dosage form via a specific vehicle, e.g. a prefabricated foam product (e.g. polypropylene foam). Still, the above technical solutions are not applicable to any type of active ingredients, do not accommodate any loading rate, and are difficult to carry out. Thus, there is still a need for another inherent sustained release form which provides improved properties and bioavailability.

Particularly, there is a need for a form that is immediately floating into the gastric juice, in order to avoid any premature emptying through the pylorus as it is the case in the existing swellable forms until they have reached the appropriate size. It should also stay longer into the stomach for a prolonged release of the drug, a better bioavailability and an optimized therapeutic efficiency of the drug. In addition, since many sustained release technologies already exist but are only designed for the administration of specific active ingredients, there is still a need to provide a sustained release form which is suitable for the delivery of different drugs and at different possible concentrations. Finally, considering the complexity of the technology of existing forms, there is still a need for systems that can be easily manufactured at an industrial scale.

SUMMARY

One aspect of the invention relates to a process for making an oral solid gastro-retentive dosage form, comprising the steps of:
(i) providing a powder mixture comprising an hydrophobic powder;
(ii) overgranulating this powder mixture with a granulating solution into an overgranulated paste;
(iii) drying said paste into a solid.

According to one embodiment, the invention provides a process wherein the active ingredient is added into the starting powder of step (i) and/or the granulating solution of step (ii), preferably into the starting powder of step (i) and/or is laid on the solid obtained at step (iii).

According to another embodiment, the invention provides a process wherein the paste is laid on a core. According to another embodiment, the invention provides a process wherein a binder is added with the starting material in step (i) and/or the granulating solution of step (ii), preferably into the starting powder of step (i). According to another embodiment, the invention provides a process further comprising the step (iv) of kneading the overgranulated paste of step (ii) prior to step (iii). According to another embodiment, the invention provides a process further comprising the step (v a) of moulding the resulting composition of step (ii) or (iv), prior to the drying step (iii), or the step (V b) of coating the resulting paste (ii) or (iii) on a core. According to another embodiment, the invention provides a process wherein the ratio solution: powder in step (ii) is at least 0.2:1, preferably in the range of about 0.3:1 to about 3:1, more preferably of about 0.7:1 to about 2:1.

According to another embodiment, the invention provides a process wherein the granulating solution is an aqueous solution, an organic solvent, a hydrophobic liquid, and preferably water. According to another embodiment, the invention provides a process wherein the hydrophobic powder comprises one or more highly lipophilic excipients selected from the group consisting of hydrophobic dusty powders and lipidic excipients. According to another embodiment, the invention provides a process wherein the one or more highly lipophilic excipients are selected from the group consisting of talc, hydrophobic silica, magnesium stearate and fatty acid, preferably talc, stearic acid and mixtures thereof.

According to another embodiment, the invention provides a process wherein the dosage form comprises:
from 0.01 to 90%, preferably 40 to 90% of active ingredient;
from 1 to 60%, preferably 5 to 50% of lipophilic excipient; and optionally;
from 1 to 20%, preferably 2 to 10% of binder.

According to another embodiment, the invention provides a process wherein the dosage form has a density below 1, preferably below 0.9 and more preferably below 0.8. According to another embodiment, the invention provides a process wherein the dosage form has a porosity of from 10 to 80% and preferably of from 20 to 70% of the volume of the form.

According to another embodiment, the invention provides a process wherein the active ingredient is selected from the group consisting of AIDS adjunct agents, alcohol abuse preparations, Alzheimer's disease management agents, amyotrophic lateral sclerosis therapeutic agents, analgesics, anesthetics, antacids, antiarythmics, antibiotics, anticonvulsants, antidepressants, antidiabetic agents, antiemetics, antidotes, antifibrosis therapeutic agents, antifungals, antihistamines, antihypertensives, antiinfective agents, antimicrobials, antineoplastics, antipsychotics, antiparkinsonian agents, antirheumatic agents, appetite stimulants, appetite suppressants, biological response modifiers, biologicals, blood modifiers, bone metabolism regulators, cardioprotective agents, cardiovascular agents, central nervous system stimulants, cholinesterase inhibitors, contraceptives, cystic fibrosis management agents, deodorants, diagnostics, dietary supplements, diuretics, dopamine receptor agonists, endometriosis management agents, enzymes, erectile dysfunction therapeutics, fatty acids, gastrointestinal agents, Gaucher's disease management agents, gout preparations, homeopathic remedy, hormones, hypercalcemia management agents, hypnotics, hypocalcemia management agents, immunomodulators, immunosuppressives, ion exchange resins, levocarnitine deficiency management agents, mast cell stabilizers, migraine preparations, motion sickness products, multiple sclerosis management agents, muscle relaxants, narcotic detoxification agents, narcotics, nucleoside analogs, non-steroidal anti-inflammatory drugs, obesity management agents, osteoporosis preparations, oxytocics, parasympatholytics, parasympathomimetics, phosphate binders, porphyria agents, psychotherapeutic agents, radio-opaque agents, psychotropics, sclerosing agents, sedatives, sickle cell anemia management agents, smoking cessation aids, steroids, stimulants, sympatholytics, sympathomimetics, Tourette's syndrome agents, tremor preparations, urinary tract agents, vaginal preparations, vasodilators, vertigo agents, weight loss agents, Wilson's disease management agents, and mixtures thereof and preferably is selected from the group consisting of abacavir sulfate, abacavirsulf ate/ lamivudine/zidovudine, acetazolamide, acyclovir, albendazole, albuterol, aldactone, allopurinol BP, Aluminium carbonate, Aluminium hydroxide, amoxicillin, amoxicillin/clavulanate potassium, amprenavir, artesunate, atovaquone, atovaquone and proguanil hydrochloride, atracurium besylate, barium sulfate, beclomethasone dipropionate, berlactone betamethasone valerat, betaïne, Bismuth subsalicylate, bupropion hydrochloride, bupropion hydrochloride SR, Calcium carbonate, carvedilol, caspofungin acetate, carbamazepin, cefaclor, cefazolin, ceftazidime, céfuroxime, chlorambucil, chloroquin, chlorpromazine, cimetidine, cimetidine hydrochloride, ciprofloxacine, cisatracurium besilate, clobetasol propionate, co-trimoxazole, colfoscerilpalpitate, dextroamphetamie sulfate, dioxin, dihydroxyartemisinin, doxycycline, enalapril maleat, epoprostenol, esomepraxole magnesium, fluticasone propionate, furosemide, gabapentin, glitazones, Hydrotalcite hydrochlorothiazide/triamterene, lamivudine, lamotrigine, levodopa, lithium carbonate, lomefloxacine, losartan potassium, Magnesium aluminate monohydrate melphalan, mercaptopurine, mefloquine mesalazine, metformine, morphin, mupirocin calcium cream, nabumetone, naratriptan, norfloxacine, ofloxacine, omeprazole, ondansetron hydrochloride, ovine, oxiconazole nitrate, paroxetine hydrochloride, pefloxacine, piroxicam, prazodin, prochlorperazine, procyclidine hydrochloride, pyrimethamine, ranitidine bismuth citrate, ranitidine hydrochloride, repaglinide, rofecoxib, ropinirole hydrochloride, rosiglitazone maleat, salmeterol xinafoate, salmeterol, fluticasone propionate, Sodium bicarbonate, sterile ticarcillin disodium/clavulanate potassium, simeticon, simvastatin, spironolactone, statins, succinylcholine chloride, sumatriptan, thioguanine, tirofiban hydrochloride, topotecan hydrochloride, tramadol, tranylcypromine sulfate, trifluoperazine hydrochloride, valacyclovir hydrochloride, vinorelbine, zanamivir, zidovudine, zidovudine or lamivudine, corresponding salts thereof, or mixtures thereof.

Another aspect of the invention relates to a dosage form obtainable by the process according to any of the preceding claims. Another aspect of the invention relates to a monolithic oral solid dosage form comprising an API and having intrinsic porosity and having a density below 1, preferably below 0.9 and more preferably below 0.8. Another aspect of the invention relates to an oral solid dosage form comprising a monolithic core, and/or at least one outer layer comprising an API, having intrinsic porosity and a density below 1, preferably below 0.9 and more preferably below 0.8. According to another embodiment, the invention provides a monolithic oral solid dosage form wherein the monolithic core and/or at least one outer layer has a porosity of from 10 to 80%, preferably of from 20 to 70% of the volume of the form.

According to another embodiment, the invention provides a solid oral dosage form comprising one or more highly lipophilic excipients and optionally further adjuvants. According to another embodiment, the invention provides a solid oral dosage form wherein the one or more highly lipophilic excipients are selected from the group consisting of hydrophobic dusty powders and lipidic excipients. According to another embodiment, the invention provides a solid oral dosage form wherein the one or more highly lipophilic excipients are selected from the group consisting of talc, hydrophobic silica, magnesium stearate and stearic acid. According to another embodiment, the invention provides a solid oral dosage form wherein the API is present in an amount of about 0.1% to about 90%, preferably of about 30% to about 80% and more preferably of about 50% to about 80% of the total weight composition.

According to another embodiment, the invention provides a solid oral dosage form further comprising one or more swellable excipients, gas generating agents, bioadhesives agents, or combinations thereof. According to another embodiment, the invention provides a solid oral dosage form wherein the swellable excipients are selected from the group consisting of hydroxymethylcellulose, hydroxyethylcellulose, hydroxypropyl methylcellulose having molecular weight from 2,000 to 2,000,000, carboxyvinyl polymers, polyvinyl alcohols, glucans, scleroglucans, chitosans, mannas, galactomannans, xantangums, carrageenans, amylase, alginic acid and salts thereof, acrylates, methacrylates, acrylic/methacrylic copolymers, polyanhydrides, polyamino acids, methyl vinyl ethers/maleic anhydride copolymers, carboxymethylcellulose and derivatives thereof, ethylcellulose, methylcellulose and derivatives of cellulose in general, superporous hydrogels in general and mixtures thereof. According to another embodiment, the invention provides a solid dosage oral form wherein the gas generating agents are selected from the group consisting of sodium hydrogen carbonates, optionally in combination with acids. According to another embodiment, the invention provides a solid oral dosage form, in the form of a moulded tablet, a multiple unit system, or a microcapsule. According to another embodiment, the invention provides a oral dosage form having a dissolution in 1000 mL of a 0.1 N HCl solution at pH 1.2 using USP type II method basket 10 Mesh at 150 rpm and a sinker, of no more than 80% after two hours, preferably of no more than 70% after two hours and more preferably of no more than 60% after two hours.

DETAILED DESCRIPTION

Granulating techniques are extensively used in industry and particularly for the preparation of pharmaceutical dosage forms. Indeed, since the components are often available as a powder, there is a need for the processing thereof, especially for the mixing with other solid excipients. It is acknowledged that granulation enhances the flow properties of the powder blends, decreases the dust formation resulting from their handling and provides the desired cohesion for compaction. Wet granulation, melt granulation, fluid bed granulation, dry mixing, liquid binder addition or high viscosity binders addition are some of these granulation techniques known to man skilled in the art. To perform a wet granulation for example, liquid solvents having low viscosity (usually water) and possibly containing binders are added to the bulk powder in a fluidized bed or a high shear mixer or impeller mixer, so that the solid particles can link to each other and form agglomerates and granules.

Figure 1:
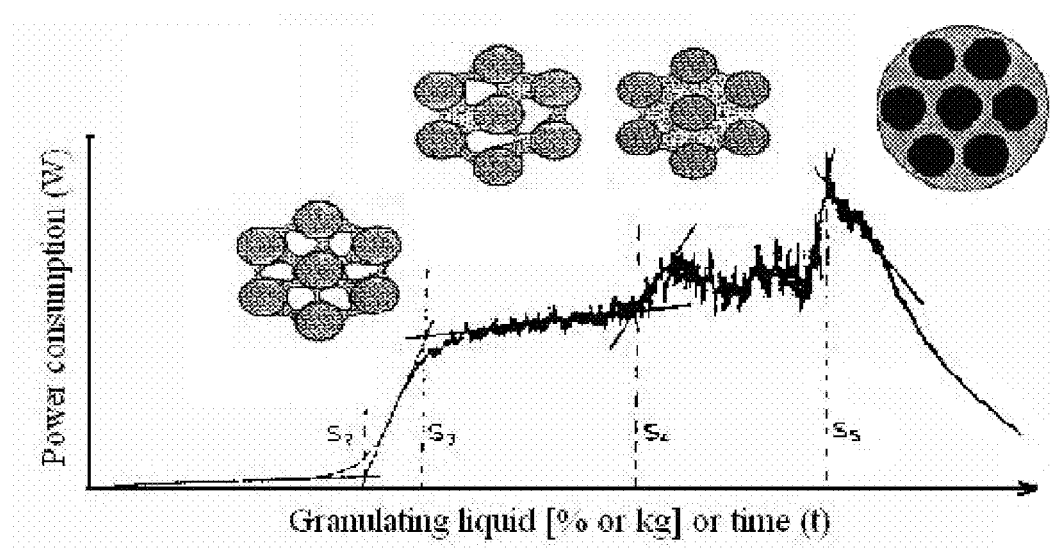
FIG. 1 represents the evolution of granulated particles comparatively with the add of the wetting agent and the overgranulated state (droplet state), during a granulation process.

The granulation phenomenon is represented in FIG. 1, showing the formation of bridges between the solid particles with the increase of quantities of the granulating solution, the saturation which is reached once the interparticular void spaces have been filled up (step IV), and finally the overgranulated state with the solid system turning into liquid. Each step represents a progressive increase in the moisture content, agglomeration mechanism is a gradual change from a triphasic stage (air-liquid-solid) in which granules are in pendular (I) and funicular (II) states to a biphasic (liquid-solid) in which the granules are in the capillary (III) and droplets (IV) state. The granulating parameters are therefore closely controlled at any of the design and operation stages of the manufacturing process, to avoid that the material becomes irremediably lost as soon as it reaches the critical granulating point. Overgranulating is carefully avoided in the pharmaceutical industry, as it is associated with a loss in active material.

The invention is based on the surprising finding that the resulting overgranulated materials, after that the granulating liquid was extracted to dryness, showed advantageous intrinsic low density and intrinsic high porosity. Thus, what was yet considered as wasted material may in fact serve in the manufacture of a floating sustained release dosage form, considering its inherent low density and high open porosity after evaporation to dryness. These advantageous characteristics result from the incorporation of air into the mass of the material via the overgranulation phenomena (either directly as air or indirectly through evaporation of entrapped water). The final solid dosage form has thus improved properties.

A first aspect of the invention is directed to a monolithic solid dosage form comprising an active ingredient (API), and having both intrinsic open porosity and low density. Examples of suitable API without being limitative may be any relating to one or more of the: AIDS adjunct agents, alcohol abuse preparations, Alzheimer's disease management agents, amyotrophic lateral sclerosis therapeutic agents, analgesics, anesthetics, antacids, antiarythmics, antibiotics, anticonvulsants, antidepressants, antidiabetic agents, antiemetics, antidotes, antifibrosis therapeutic agents, antifungals, antihistamines, antihypertensives, antiinfective agents, antimicrobials, antineoplastics, antipsychotics, antiparkinsonian agents, antirheumatic agents, appetite stimulants, appetite suppressants, biological response modifiers, biologicals, blood modifiers, bone metabolism regulators, cardioprotective agents, cardiovascular agents, central nervous system stimulants, cholinesterase inhibitors, contraceptives, cystic fibrosis management agents, deodorants, diagnostics, dietary supplements, diuretics, dopamine receptor agonists, endometriosis management agents, enzymes, erectile dysfunction therapeutics, fatty acids, gastrointestinal agents, Gaucher's disease management agents, gout preparations, homeopathic remedy, hormones, hypercalcemia management agents, hypnotics, hypocalcemia management agents, immunomodulators, immunosuppressives, ion exchange resins, levocarnitine deficiency management agents, mast cell stabilizers, migraine preparations, motion sickness products, multiple sclerosis management agents, muscle relaxants, narcotic detoxification agents, narcotics, nucleoside analogs, non-steroidal anti-inflammatory drugs, obesity management agents, osteoporosis preparations, oxytocics, parasympatholytics, parasympathomimetics, phosphate binders, porphyria agents, psychotherapeutic agents, radio-opaque agents, psychotropics, sclerosing agents, sedatives, sickle cell anemia management agents, smoking cessation aids, steroids, stimulants, sympatholytics, sympathomimetics, Tourette's syndrome agents, tremor preparations, urinary tract agents, vaginal preparations, vasodilators, vertigo agents, weight loss agents, Wilson's disease management agents, and mixtures thereof.

Without being limitative, suitable active ingredients may thus be one or more selected from: abacavir sulfate, abacavirsulfate/lamivudine/zidovudine, acetazolamide, acyclovir, albendazole, albuterol, aldactone, allopurinol BP, amoxicillin, amoxicillin/clavulanate potassium, amprenavir, artesunate, atovaquone, atovaquone and proguanil hydrochloride, atracurium besylate, beclomethasone dipropionate, berlactone betamethasone valerat, betaïne, bupropion hydrochloride, bupropion hydrochloride SR, carvedilol, caspofungin acetate, carbamazepin, cefaclor, cefazolin, ceftazidime, céfuroxime, chlorambucil, chlorpromazine, cimetidine, cimetidine hydrochloride, ciprofloxacine, cisatracurium besilate, clobetasol propionate, co-trimoxazole, colfosceril-palpitate, dextroamphetamie sulfate, dihydroxyartemisinin, dioxin, doxycycline, enalapril maleat, epoprostenol, esomepraxole magnesium, fluticasone propionate, furosemide, gabapentin, glitazones, hydrochlorothiazide/triamterene, lamivudine, lamotrigine, levodopa, lithium carbonate, lomefloxacine, losartan potassium, melphalan, mercaptopurine, mesalazine, metformine, morphin, mupirocin calcium cream, nabumetone, naratriptan, norfloxacine, ofloxacine, omeprazole, ondansetron hydrochloride, ovine, oxiconazole nitrate, paroxetine hydrochloride, pefloxacine, piroxicam, prazodin, prochlorperazine, procyclidine hydrochloride, pyrimethamine, ranitidine bismuth citrate, ranitidine hydrochloride, Repaglinide, rofecoxib, ropinirole hydrochloride, rosiglitazone maleat, salmeterol xinafoate, salmeterol, fluticasone propionate, sterile ticarcillin disodium/clavulanate potassium, simeticon, simvastatin, spironolactone, statins, succinylcholine chloride, sumatriptan, thioguanine, tirofiban hydrochloride, topotecan hydrochloride, tramadol, tranylcypromine sulfate, trifluoperazine hydrochloride, valacyclovir hydrochloride, vinorelbine, zanamivir, zidovudine, zidovudine or lamivudine, corresponding salts thereof, or mixtures thereof.

Preferably, the active ingredient is one or more of the API chosen from the group consisting of the antibacterial agents, or the antibiotics, such as norfloxacine, ofloxacine, ciprofloxacine, pefloxacine, lomefloxacine, quinolones, ceflaclor or pharmaceutically acceptable salts thereof, the analgesics, such as tramadol, morphine or pharmaceutically salts thereof, the anti-acids such as simethicones, and the anti-diabetes, such as metformin or pharmaceutically acceptable salts thereof. These drugs exhibit higher therapeutical effects when absorbed in the upper intestine and stomach. A most preferred API would be those that provide beneficial therapeutic effects for urinary infections or diseases, such as ciprofloxacine, lomefloxacine, ofloxacine, or pharmaceutically acceptable salts thereof, or diabetes, such as metformine, or any of their pharmaceutically acceptable salts.

Unlike the existing sustained release systems which are designed for a specific drug to be administered, the solid dosage form of the invention may advantageously be associated with any suitable active ingredient (API) that provides a therapeutical effect. The invention is ideal for oral delivery of a wide range of molecules characterized by a narrow absorption window and is particularly effective with water soluble and poorly soluble molecules with different physicochemical properties and molecular sizes.

The amount of the active ingredient in the pharmaceutical compositions of the present invention will be a therapeutically effective amount. The dosage form of the invention allows high drug loads compared to the existing sustained release forms and a therapeutically effective amount will generally be an amount within the range of from about 0.01 to about 90%, preferably within the range of from about 40 to about 90% and more preferably of from about 50 to about 85% by weight of the composition. It is understood that higher or lower weight percentages of the active ingredient may be present in the pharmaceutical compositions. By "therapeutically effective amount" as used herein is meant an amount of active component in the pharmaceutical compositions of the present invention which is effective to beneficially treat the patient in need thereof. The intrinsic properties of the solid dosage form according to the invention result from the overgranulation of one or more lipophilic excipients, followed by drying.

As used herein, "lipophilic" in reference to the excipients, is intended to mean any sparingly soluble component that is commonly used in formulation and typically include components with little water solubility or with water insolubility. Without being limitative, an example of a typical little water solubility is less than 1 mg/l. Suitable lipophilic excipients are not particularly limited, as the invention is surprisingly capable of providing materials showing intrinsic low density and high porosity from the overgranulation of a wide range of different excipients or of mixtures thereof. Preferably, these lipophilic excipients also have hydrophobic properties as they are not capable of binding at all to water molecules. Such excipients are often apolar or show a low polarity, which means that they also do not allow electrostatic interactions with water (such as Keesom forces).

Particular non limiting examples of these excipients are hydrophobic dusty powders, such as silicas, talc, magnesium stearate, as well as general lipidic excipients such as fatty esters, fatty acid, among which stearic acid, or any fatty acid that is solid at room temperature, or mixture thereof. Hydrophobic silica, talc and fatty acid are particularly preferred. Hydrophobic silica possesses physical properties that are useful in a number of applications requiring a high degree of dispersibility, including its use in toner compositions, as anti-blocking agents, as adhesion modifiers, and as polymer fillers. Untreated silica particles are hydrophilic due to the presence of silanol groups on the surface of the untreated silica particles. Therefore, different degrees of hydrophobicity may be obtained as a result of treatments of the silica, such as with reagents introducing functional apolar groups onto the silica surface, resulting in the reduction the hydrophilic nature of the particles.

Talc, is a mineral composed of hydrated magnesium silicate having the formula $H_2Mg_3(SiO_3)_4$ or $Mg_3Si_4O_{10}(OH)_2$. In loose form it is known as talcum powder and finds uses in cosmetic products, as a lubricant, as a filler in paper manufacture, but also as a food or pharmaceutical additive.

The lipophilic material is generally provided as a powder or "impalpable dust". Powder size $d_{50}$ is generally from 10 nm to 500 µm, preferably from 10 to 50 nm and most preferably of from 10 to 20 nm. For example, a mixture of talc and hydrophobic silica having a powder size of 15 nm was found to be particularly suitable. The amount of lipophilic excipients will generally be an amount within the range of from about 0.01 to about 90%, preferably within the range of from about 1 to about 60% and more preferably of from about 5 to about 50% by weight of the composition. Indeed proportions of about 5 to about 40%, and even down to about 20% permit high quantities of active ingredient to be loaded in the form and still provide intrinsic properties for the floatability of the final dosage form.

Eventually, further adjuvants may come into the composition of the present form, and may include any of the following components: binder, diluent, lubricant, anti-static agent and optionally other auxiliary agents such as sustained release agents, gelifying agents, disintegrating agents, surfactants. Adjuvants may be of any type, since it is the one or more lipophilic excipients which principally provide through the overgranulation phenomena the resulting floating material. Adjuvants that are particularly useful are those that will create cavities within the structure once dried after the overgranulation step, and thus, provide a higher porosity to the final form. Examples of such adjuvants are for example, swellable excipients, gelifying agents, disintegrant agents, or diluents.

In the framework of this invention, the expression "binder" means any excipients which enhances the linkage between particles and include without being limitative: cellulose derivatives such as methylcellulose, carboxymethylcellulose, carboxypropylcellulose, hydroxypropylcellulose and hydroxypropylmethylcellulose (HPMC), crystalline cellulose, starches or pregelatinized starch, polyvinyl alcohol, polyvinylpyrrolidone (PVP), pullulan, dextrin, acacia, gums, excipients and the like, and combination thereof. PVP is the preferred binder. The amount of binder used in the composition may vary within broad limits, for example from 1 to 20% by weight, preferably from 2 to 10%.

In the framework of this invention, the expression "diluent" means any excipients which acts to dilute the formulation without undergoing a chemical reaction with the formulation components. A diluent of the invention includes generally inert carriers or vehicles, be it crystalline or amorphous. Examples of such diluents are derivatives of sugars, such as lactose, saccharose, mannitol, etc., and mixtures thereof. Hydrolyzed starch (malto-dextrine) can be used, preferably in low amounts.

Certain examples of excipients may be at the same time binder and disintegrants. Further excipients are disclosed in *Handbook of Pharmaceutical excipients*, $2^{nd}$ Ed., 1994, American Pharmaceutical Association, Washington, ISBN 0 91730 66 8, by Wade A., Weller P J.).

Since it is the one or more lipophilic excipients(s) that allow(s) providing an overgranulated material having high porosity and low density, the prepared solid dosage system containing the API may be of different forms. According to one preferred embodiment of the invention, the API is dispersed within the form having intrinsic low density and high porosity. A solid powder of the one or more active ingredient to be administered is directly admixed with the lipophilic excipients (preferably with a binder) prior to the granulation step. Alternatively, a liquid API may be used, either added directly or into the wetting solvent.

One benefit of this embodiment is that the API powder provides supplementary starting material in addition to the lipophilic excipients in the preparation of highly porous forms by granulation, especially if it is a hydrophobic active ingredient. In such case, the API also has the role of a lipophilic excipient. In addition, the API is homogeneously dispersed within the final dosage form which exhibits a constant and controlled release profile into the body. The API may also be hydrophilic. This will not influence the final properties of the dosage form, provided appropriate lipophilic excipients and amounts thereof are used.

According to another embodiment, the API is contained in an outer layer surrounding a core having the advantageous intrinsic properties of the dosage form, or eventually in one or more additional layers. Thereby, the release of the drug may be sustained or controlled depending on the structure of the dosage form, and the type of ingredients and/or adjuvants that are used.

In another embodiment, one API may be dispersed within the dosage form while another is present in an outer layer.

Preferably, the API in the outer layer is in a form that is an immediate release form. One example would be a dosage form with an antibiotic (eg. Ciprofloxacin) in the core and a benzimidazole (eg. Omeprazole) in the outer immediate release layer. In addition, in accordance with the preferred embodiment where the API is dispersed and processed with the lipophilic excipients, the resulting overgranulated material provided with high porosity and low density may be used to manufacture either the solid dosage form in its whole, or the core. Indeed, according to these different embodiments, any oral dosage form comprising this material will have the required floating properties.

Figure 3:
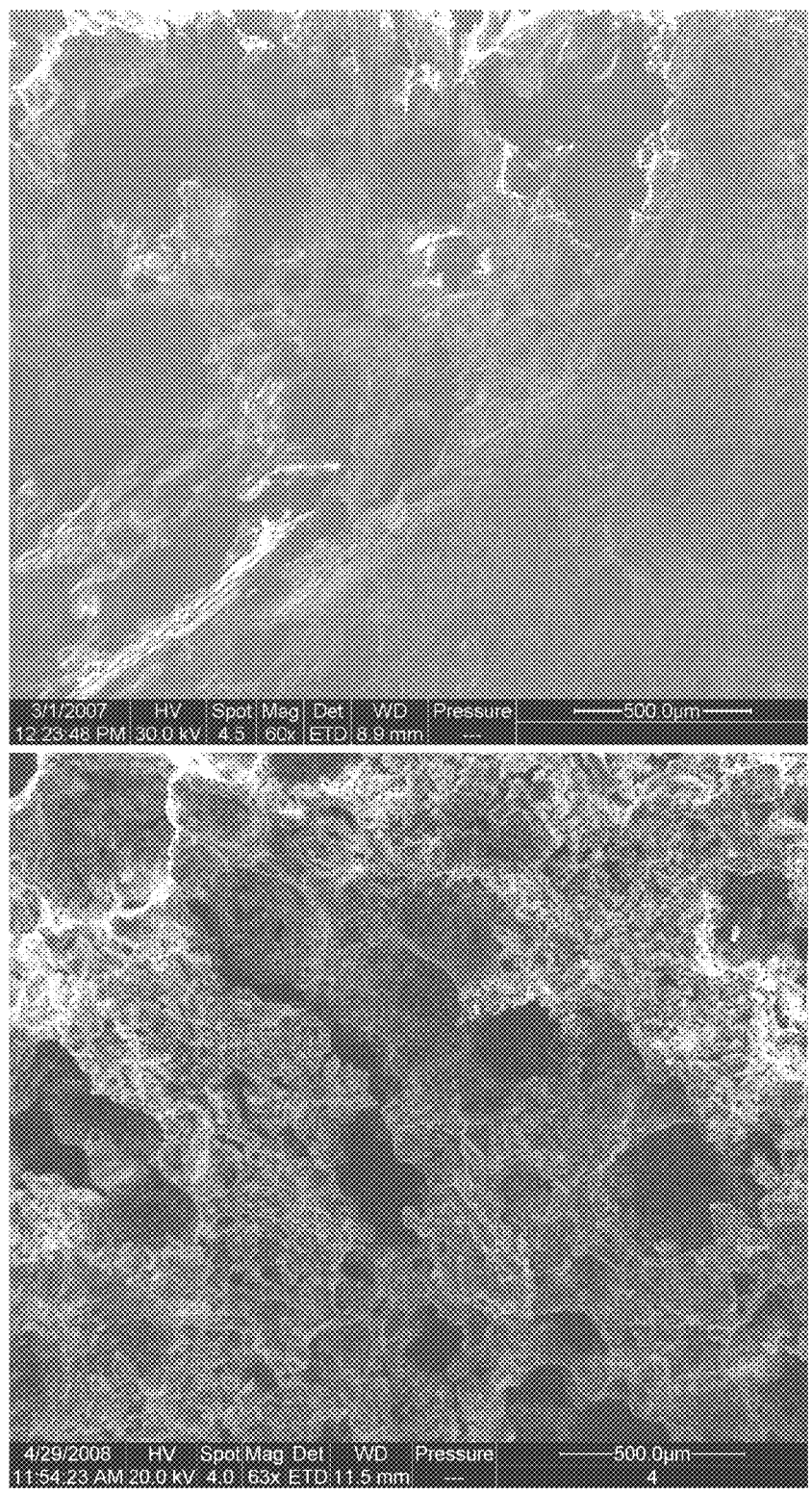
FIG. 3 is a magnified microphotography of the porous solid dosage forms No 1 and No 2 prepared according to example 1.

The capability to float into the stomach in the gastric juice is usually reached for devices having a density below 1,004. The density provided by the process to the dosage form is less than about 1, preferably below 0.9 and more preferably below 0.8, depending on the formulation and how far the overgranulation process is performed and the quantity of air introduced into the overgranulated material prior to the drying of the granulating solution. Preferably, a dosage according to the invention has a density of about 0.6, and more preferably of about 0.4. Photographs of FIG. 3 illustrate the inherent low density of a porous overgranulated and dried material due to the numerous cavities that were created within the structure of the material.

Figure 2:
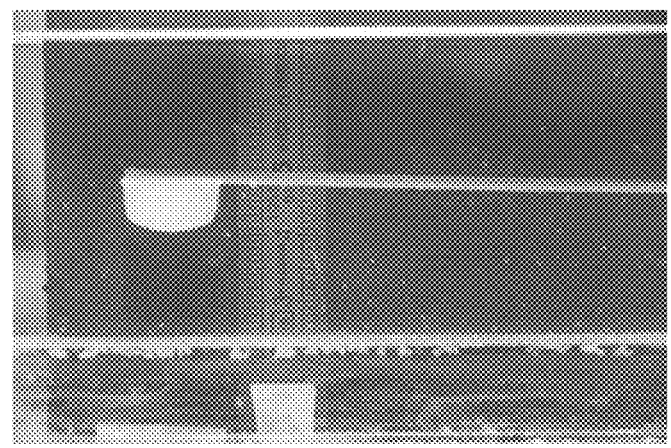
FIG. 2 represents photographs of a test for determining the density of solid dosage forms according to the invention.
Figure 2:
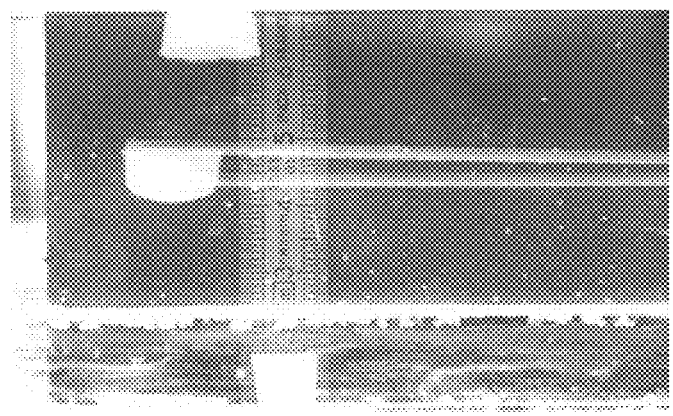

The density can be determined by sinking a solid dosage oral form according to the invention into a liquid having a pH=1.2, or water, or gastric juice or any other liquid of known density. The solid dosage form is sunk at an initial position under a flexible indicator (by an horizontal arrow and a ruler in FIG. 2) and the deviation it creates allows the calculation of its density according to the following formula:

$$\rho_c = \frac{\rho_f}{1 - \frac{Ewh^3}{4gL^3}\frac{\delta_c}{m_c}}$$

wherein: $\rho_c$ is the tablet density (unit: kg/m$^3$); $\rho_f$ is the liquid density (unit: kg/m$^3$); $m_c$ is the tablet weight (unit: kg); $\delta_c$ is the powder deviation induced by the presence of the tablet (unit: m); L is the truss length (unit: m); w is the truss width (unit: m); h is the truss Thickness (unit: m); E is the coefficient of elasticity of solid (Young's modulus unit: Pa)

The porosity may be calculated from the comparison of the apparent volume with the real volume of the dosage form. While the previous density calculation provides the apparent volume $V_1$ (volume of the matrix with the volume of the pores in the pellet), another measure with a helium pycnometer provides the real volume $V_2$ (without the volume of the pores). Thus, the volume of the pores is given by: $V_p = V_1 - V_2$. The porosity is reached by the ratio $V_p/V_1$. Porosity may represent from 10 to 80% of the total volume of the form, and preferably of from 20 to 70% of its volume. The material with inherent low density and high porosity is also monolithic, which refers to a structure which is solidly uniform. This can be observed in the photographs of FIG. 3, wherein the structure is not edified from particles or granulates, but rather stands as a single piece.

The solid dosage form of the invention may further comprise swellable excipients, gas generating and/or bioadhesive agents. Since it possesses inherent low density, it will advantageously float immediately into the stomach after swallowing and thus, does not rely on the use of additional excipients. These may however improve the time residence of the system into the stomach and thus, the bioavailability of the drug to be administered.

Swellable excipients, once in contact with the gastric juice increase in size. The floating capability of the dosage form directly after swallowing, allows the swellable excipients to gradually reach the desired size without risking premature emptying through the pylorus. Therefore, there is no limiting swelling rate for suitable excipients that can be used in the present invention. They may be selected from the group consisting of hydroxymethylcellulose, hydroxyethylcellulose, hydroxypropyl methylcellulose having molecular weight from 2,000 to 2,000,000, carboxyvinyl polymers, polyvinyl alcohols, glucans, scleroglucans, chitosans, mannas, galactomannans, gums, xantan gums, carrageenans, amylase, alginic acid and salts thereof, acrylates, methacrylates, acrylic/methacrylic copolymers, polyanhydrides, polyamino acids, methyl vinyl ethers/maleic anhydride copolymers, carboxymethylcellulose and derivatives thereof, ethylcellulose, methylcellulose and derivatives of cellulose in general, superporous hydrogels in general and mixtures thereof.

Preferably, they would be useful as an outer layer surrounding a core having intrinsic low density and high porosity, and optionally may contain dispersed therein the active ingredient to be released. The layers may further contain gas forming agent in order to improve the buoyancy. These agents, when in contact with an aqueous media, form a non toxic gas, decrease even more the density of the pharmaceutical form, and provide supplementary floating properties to prolong the gastric residence time into the stomach. Examples of gas forming agents are sodium hydrogen carbonates employed individually or in combination with acids. Bioadhesive agents may also be incorporated on the outer layer of the solid form, allowing the pharmaceutical form positioning and adhesion to the mucosa of the stomach or the upper gastrointestinal tract.

The invention provides an oral solid dosage form having an enhanced solubility in acidic medium such as the gastric juice. Preferably, the composition exhibits a dissolution profile in hydrochloric acid 0.1 N buffer at pH 1.2, using the US Pharmacopoeia type II method at 150 rpm and using a sinker instead of a mesh, of no more than 80% after 2 hours, preferably no more than 70% after 2 hours and more preferably no more than 60%. The sinker is used in order to conform the USP standards to the case of the present floating forms and ensure the immersion of the form into the liquid. Thus, this characteristic allows an improved bioavailability of the drug to be released.

Another aspect of the invention is to provide a process to prepare the solid dosage form of the invention. The intrinsic properties are provided by the overgranulation step of a powder mixture of part or all of the components, and at least of the lipophilic excipients, followed by a drying step.

A first step of the process is to provide such powder mixture comprising the lipophilic excipients in a powder form. The powder may further contain the binder. They are admixed in the desired proportions and eventually dry blended to provide a homogeneous powder mixture. In this case, it may be preferred that the rotating speed is adapted to avoid the dispersion of the lipophilic excipients onto the walls of the vessel. Preferably, if the active ingredient is intended to be dispersed within the intrinsic low density and highly porous material, it should also be loaded into the powder mixture with optionally the other adjuvants.

A second step of the process is the granulation of the previous mixture with a wetting solution, preferably an aqueous solution, to be performed until the overgranulation state is reached and eventually continued after this point. Suitable installation may be any conventional setting to the man skilled in the art, such as a High Shear Mixer with an impeller. Optionally, a chopper can advantageously be adapted to the installation of a Shear Mixer to destroy the biggest agglomerates before reaching the overgranulated state.

A particularly suitable aqueous solution is water although any aqueous solution may be used. Any other conventional granulation liquids may be suitable, such as organic solvents, or hydrophobic materials that are liquid at room temperature. The wetting solution can comprise (albeit this is not preferred) part or, all of the binder and/or part or all of the API, if it is water soluble and/or part or all of a surfactant if any. The weight ratio of solution: powder to reach is strongly dependant of the global solubility of the powder mixture and is generally higher than 0.3, and typically comprised in the range of about 0.3:1 to about 3:1, preferably of about 0.7:1 to about 2:1. It is worth to remind that traditional granulation is performed with a rather low liquid: powder ratio, typically of from 0.1:1 to 0.3:1. Such a low ratio is used to avoid overgranulation in a typical granulation method, where overgranulation is exactly what is looked for in the instant process.

According to a preferred method of granulation, the aqueous solution is added drop wise. The mixing is then continued until the mixture turns into the overgranulated state. The granulation should preferably be performed at a sufficiently high (impeller) rotating rate to allow the incorporation of air into the mass of the overgranulated material, preferably of from 150 to 1500 rpm, although lower or higher rates may be suitable. Thus, the highest is the rotating rate, the lowest density will intrinsically be given to the resulting solid dosage form. The rotating speed and the wetting liquid addition rate can be adapted one to the other. A higher rotating speed with a lower addition rate will incorporate more air.

Typically, the granulation step is achieved once the obtained paste shows a resistance of about 4 to about 8% of the torque usually just after that a peak appears when monitoring the torque during the granulation or just after a further kneading step, once the critical amount of wetting solution is reached. This critical amount of granulating fluid usually corresponds to about 80% by weight of the weight of the starting material. The particulate system is then completely filled with liquid leading to coarse granules. The liquid saturation is equal to 100% at this point (See FIG. 1, S5). In this last phase, after the peak apparition, the system passes into a suspension. This suspension becomes more fluid as more granulating liquid is added after the critical point, which may be adapted to provide the overgranulated material with an appropriate viscosity.

The resulting material may in a further step be kneaded, to provide an overgranulated paste of the desired consistency, and to incorporate additional quantities of air into the mass. This is advantageously performed to provide higher porosity and thus a lower density to the final floating material. For example, the material may be kneaded at a rate of from 150 to 1500 rpm, although lower or higher rates may be suitable.

A last step of the process would be finally to extract the granulating solution up to dryness, to a maximum water content of about 3% of the global composition. The paste turns into a solid. This can be performed by lyophilisation methods or by any other conventional techniques to the man skilled in the art. In order to improve the porosity of the final resulting material, it may be particularly interesting to add at any stage of the process prior to the drying step a gas forming agent which will incorporate further air into the paste.

Further processing steps may be performed in order to manufacture single or multiple unit systems, or microcapsules according to conventional techniques. For example, the resulting product can be spheronized into uniform in shape and size spheres, provided with defined surface characteristics, and which are suitable for coating or transportation. Particularly, after the granulating step and prior to the extraction of the aqueous solution, the resulting material can advantageously be moulded in order to provide a final system which is directly dried in the form of a tablet or beads.

In order to facilitate the manufacturing process, further adjuvants can be added to the composition into the initial powder mixture, during the manufacture or at the end, such as lubricants, anti-static agents or glidants. In the framework of this invention, the expression "lubricant" means any excipient which ease ejection of the tablet from the tableting dye in which it is formed by compression and improves the flow properties of the composition in powder or granule. Examples of lubricants are talc, magnesium stearate and glyceryl behenate, and mixtures thereof. Therefore, the solid dosage forms of the invention can be prepared by techniques which are easily operated at an industrial scale.

EXAMPLES

Preparation of solid dosage forms according to the invention. Two different solid dosage forms of the following compositions (batchs of 100 g) were prepared according to the invention. Form No 1 comprises a hydrophilic API and form No 2 a hydrophobic API. A magnified photography of the structure dosage forms No 1 or No 2 are given in FIG. 3.

|  | API | Stearic Acid | PVP | Dusty hydrophobic powder (talc) | Density Kg/m3 |
| --- | --- | --- | --- | --- | --- |
| No 1 | Theophylline 70.00% | 10.00% | 10.00% | 10.00% | 617.32 |
| No 2 | Doxycyclin 77.5% | 5.00% | 12.5% | 5.00% | 824.72 |

Powders of API with the other excipients were loaded together in a shear mixer 4M8 granulator and blended at 150 rpm during 2 min 30 sec. Granulation was initiated at a rotating speed of 1000 rpm by adding water at a rate of 10 ml/min. The overgranulation was reached after the introduction of the 80 ml of water, thus for a solution:powder ratio of 0.8, and the resulting paste was further kneaded at 1500 rpm during 2 min 30 sec, until it showed a resistance of between 4 and 8% of the torque. The resulting material was then moulded in cells lubricated with paraffin oil. The final drying step was finally conducted in a ventilated oven at 60° C., until less than 3% of residual humidity was measured by weight loss from desiccation.

Form No 1 provides a real volume of $V_2$=0.32952 cm$^3$ and an apparent volume of $V_1$=0.7404 cm$^3$. The porosity is thus of 0.5549 and represent no less than about 55% of the total volume of the dosage form.

Figure 4:
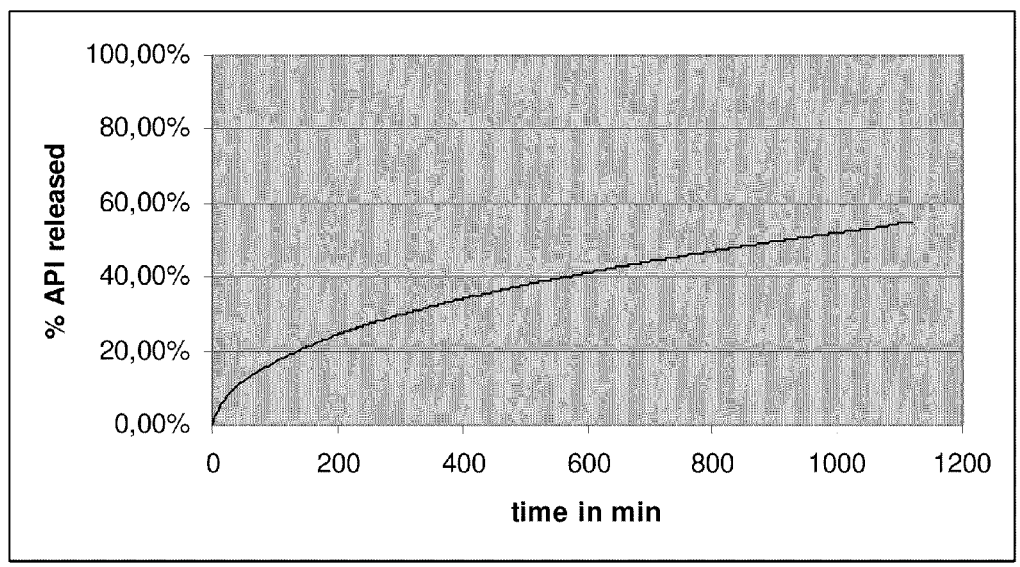
FIG. 4 shows the dissolution profiles of forms No 1 of example 1, in 1000 mL of a 0.1 N HCl medium at pH=1.2, according to USP II using a sinker at 150 rpm, at a temperature of 35° C.

Dissolution of the prepared solid dosage forms was measured using Japanese sinker system, a Dissolution test distek USP type II apparatus, the medium being EP gastric Media: 1000 mL of pH 1.2 without enzyme, a rotating speed of 150 rpm, and a dosing UV PC 2401 shimadzu spectrophotometer apparatus. The test was run over 1120 min at 35° C.±0.5° C. and showed the dissolution profile according to FIG. 4. At the end of the test, the buoyancy was investigated; the two forms present no change in their appearance and float.

It appears from the results, that the solid dosage form exhibits an improved dissolution profile compared to the existing forms, since the release is kept effective over longer periods of time. In addition, the use of a sinker provides stress conditions that are tougher than the real in vivo conditions, since the dosage form is sank into an aqueous medium instead of floating into the gastric juice.

The invention claimed is:

1. A process for making an oral solid gastro-retentive dosage form comprising from 5 to 50% by weight of hydrophobic powder said process, comprising:
   (i) providing a powder mixture comprising a hydrophobic powder;
   (ii) overgranulating this powder mixture with a granulating solution into an overgranulated paste, wherein said overgranulating comprises changing the powder mixture from a triphasic air-liquid-solid stage in which granules are in pendular and funicular states to a biphasic liquid-solid stage in which the granules are in capillary and droplet states; and
   (iii) drying the paste into a solid.

2. The process of claim 1, further comprising adding an active ingredient into at least one of the powder of step (i) and the granulating solution of step (ii).

3. The process of claim 2, wherein the active ingredient is selected from the group consisting of AIDS adjunct agents, alcohol abuse preparations, Alzheimer's disease management agents, amyotrophic lateral sclerosis therapeutic agents, analgesics, anesthetics, antacids, antiarythmics, antibiotics, anticonvulsants, antidepressants, antidiabetic agents, antiemetics, antidotes, antifibrosis therapeutic agents, antifungals, antihistamines, anti hypertensives, antiinfective agents, antimicrobials, antineoplastics, antipsychotics, antiparkinsonian agents, antirheumatic agents, appetite stimulants, appetite suppressants, biological response modifiers, biologicals, blood modifiers, bone metabolism regulators, cardioprotective agents, cardiovascular agents, central nervous system stimulants, cholinesterase inhibitors, contraceptives, cystic fibrosis management agents, deodorants, diagnostics, dietary supplements, diuretics, dopamine receptor agonists, endometriosis management agents, enzymes, erectile dysfunction therapeutics, fatty acids, gastrointestinal agents, Gaucher's disease management agents, gout preparations, homeopathic remedy, hormones, hypercalcemia management agents, hypnotics, hypocalcemia management agents, immunomodulators, immunosuppressives, ion exchange resins, levocarnitine deficiency management agents, mast cell stabilizers, migraine preparations, motion sickness products, multiple sclerosis management agents, muscle relaxants, narcotic detoxification agents, narcotics, nucleoside analogs, non-steroidal anti-inflammatory drugs, obesity management agents, osteoporosis preparations, oxytocics, parasympatholytics, parasympathomimetics, phosphate binders, porphyria agents, psychotherapeutic agents, radio-opaque agents, psychotropics, sclerosing agents, sedatives, sickle cell anemia management agents, smoking cessation aids, steroids, stimulants, sympatholytics, sympathomimetics, Tourette's syndrome agents, tremor preparations, urinary tract agents, vaginal preparations, vasodilators, vertigo agents, weight loss agents, Wilson's disease management agents, and mixtures thereof, abacavir sulfate, abacavirsulfate/lamivudine/zidovudine, acetazolamide, acyclovir, albendazole, albuterol, aldactone, allopurinol BP, aluminium carbonate, aluminium hydroxide, amoxicillin, amoxicillin/ clavulanate potassium, amprenavir, artesunate, atovaquone, atovaquone and proguanil hydrochloride, atracurium besylate, barium sulfate, beclomethasone dipropionate, berlactone betamethasone valerat, betaïne, bismuth subsalicylate, bupropion hydrochloride, bupropion hydrochloride SR, calcium carbonate, carvedilol, caspofungin acetate, carbamazepin, cefaclor, cefazolin, ceftazidime, cefuroxime, chlorambucil, chloroquin, chlorpromazine, cimetidine, cimetidine hydrochloride, ciprofloxacine, cisatracurium besilate, clobetasol propionate, co-trimoxazole, colfoscerilpalpitate, dextroamphetamie sulfate, dioxin, dihydroxyartemisinin, doxycycline, enalapril maleate, epoprostenol, esomepraxole magnesium, fluticasone propionate, furosemide, gabapentin, glitazones, hydrocalcite hydrochlorothiazide/triamterene, lamivudine, lamotrigine, levodopa, lithium carbonate, lomefloxacine, losartan potassium, magnesium aluminate monohydrate melphalan, mercaptopurine, mefloquine mesalazine, metformine, morphin, mupirocin calcium cream, nabumetone, naratriptan, norfloxacine, ofloxacine, omeprazole, ondansetron hydrochloride, ovine, oxiconazole nitrate, paroxetine hydrochloride, pefioxacine, piroxicam, prazodin, prochlorperazine, procyclidine hydrochloride, pyrimethamine, ranitidine bismuth citrate, ranitidine hydrochloride, repaglinide, rofecoxib, ropinirole hydrochloride, rosiglitazone maleate, salmeterol xinafoate, salmeterol, fluticasone propionate, sodium bicarbonate, sterile ticarcillin disodium/clavulanate potassium, simeticon, simvastatin, spironolactone, statins, succinylcholine chloride, sumatriptan, thioguanine, tirofiban hydrochloride, topotecan hydrochloride, tramadol, tranylcypromine sulfate, trifluoperazine hydrochloride, valacyclovir hydrochloride, vinorelbine, zanamivir, zidovudine, or lamivudine, corresponding salts thereof, and mixtures thereof.

4. The process according to claim 2, wherein the gastroretentive dosage form comprises from 50% to 80% by weight of active ingredient based on the total weight of the composition.

5. The process of claim 1, further comprising laying the paste on a core.

6. The process of claim 1, further comprising adding a binder into at least one of the powder of step (i) and the granulating solution of step (ii).

7. The process according to claim 1, further comprising a step (iv) of kneading the overgranulated paste of step (ii) prior to step (iii).

8. The process according to claim 7, further comprising a step (v a) of moulding the resulting composition of one of step (ii) and (iv), prior to one of: the drying step (iii) a step (v b) of coating the resulting paste of at least one step of (ii) and (iii) on a core.

9. The process according to claim 1, wherein a weight ratio of solution: powder in step (ii) is at least 0.2:1.

10. The process according to claim 1, wherein the granulating solution is selected from a group consisting of an aqueous solution, an organic solvent, a hydrophobic liquid, and water.

11. The process according to claim 1, wherein the hydrophobic powder comprises one or more lipophilic excipients selected from the group consisting of hydrophobic dusty powders and lipidic excipients.

12. The process according to claim 11, wherein the lipophilic excipients are selected from the group consisting of talc, hydrophobic silica, magnesium sterarate and stearic acid.

13. The process according to claim 1, wherein the process further comprises:
   adding an active ingredient into at least one of the powder of step (i) and the granulating solution of step (ii); and
   adding a binder into at least one of step (i) and the granulating solution of step (ii), wherein
   the hydrophobic powder comprises one or more lipophilic excipients, and the dosage form comprises:

from 0.01 to 90% of active ingredient;
from 5 to 50% of lipophilic excipient; and
from 1 to 20% of binder.

14. The process of claim 1, wherein the dosage form has a density below 1.

15. The process of claim 1, wherein the dosage form has a porosity of from 10 to 80% of the volume of the form.

16. The process according to claim 1, wherein the gastro-retentive dosage form comprises an active pharmaceutical ingredient and has intrinsic porosity and has a density below 1.

17. The process according to claim 1, wherein the gastro-retentive dosage form comprises at least one of a monolithic core, and at least one outer layer comprising an active pharmaceutical ingredient, and has intrinsic porosity and a density below 1.

18. The process according to claim 1, wherein the gastro-retentive dosage form comprises at least one of a monolithic core and at least one outer layer and has a porosity of from 10 to 80% of the volume of the form.

19. The process according to claim 1, wherein the gastro-retentive dosage form comprises a dissolution in 1000 mL of a 0.1 N HCl solution at pH 1.2 using USP type II method basket 10 Mesh at 150 rpm and a sinker, of no more than 80% after two hours.

20. A process for making an oral solid gastro-retentive dosage form comprising at least one of a monolithic core, and at least one outer layer comprising an active pharmaceutical ingredient, and having intrinsic porosity and a density below 1, said process comprising:
   (i) providing a powder mixture comprising a hydrophobic powder;
   (ii) overgranulating this powder mixture with a granulating solution into an overgranulated paste, wherein said overgranulating comprises changing the powder mixture from a triphasic air-liquid-solid stage in which granules are in pendular and funicular states to a biphasic liquid-solid stage in which the granules are in capillary and droplet states;
   (iii) drying the paste into a solid.

* * * * *